United States Patent [19]

Long et al.

[11] Patent Number: 4,783,418
[45] Date of Patent: Nov. 8, 1988

[54] METHOD OF DETERMINING THE NICOTINE CONTENT OF TOBACCO

[75] Inventors: Terence M. Long, Yatton; Joseph C. Johnson, Frampton Cotterell; Maurice Naylor, Backwell, all of England

[73] Assignee: Imperial Tobacco Limited, Bristol, England

[21] Appl. No.: 2,931

[22] Filed: Jan. 13, 1987

[30] Foreign Application Priority Data

Jan. 13, 1986 [GB] United Kingdom ................ 8600680

[51] Int. Cl.$^4$ ............................................. G01N 33/00
[52] U.S. Cl. ..................................... 436/96; 131/297
[58] Field of Search ........................... 436/96; 131/297

[56] References Cited

U.S. PATENT DOCUMENTS

| 3,115,883 | 12/1963 | Morrell | 131/297 |
| 3,338,248 | 8/1967 | Pavia | 131/297 |
| 4,068,671 | 1/1978 | Casey | 131/297 |
| 4,215,706 | 8/1980 | Larson et al. | 131/297 |
| 4,236,532 | 12/1980 | Schweizer et al. | 131/335 |
| 4,286,604 | 9/1981 | Ehretsmann et al. | 131/359 |
| 4,419,452 | 12/1983 | Imai et al. | 436/96 |
| 4,579,858 | 4/1986 | Ferneö et al. | 131/347 |

OTHER PUBLICATIONS

W. R. Harvey and A. M. Palmer, Tob. Sci., Mar. 5, 1975, pp. 61-63.
Collins et al., Tob. Abst., vol. 13, No. 1 (13), 1969.
J. A. Allen and W. F. Pickering, Aust. J. Appl. Sci., 12, pp. 42-55, 1961.

*Primary Examiner*—Michael S. Marcus
*Assistant Examiner*—Timothy M. McMahon
*Attorney, Agent, or Firm*—Larson and Taylor

[57] ABSTRACT

A method of determining on a discrete analyzer the nicotine content of tobacco or a smoking-related product by preparing an aqueous extract of a sample of tobacco or smoking-related product, pre-reacting the extract with an acidic buffered solution of pH not more than 6 for at least two minutes, reacting the pre-reacted extract in the discrete analyzer with aniline and cyanogen bromide, measuring the intensity of yellow coloration generated, and comparing said intensity with that produced by a nicotine standard to determine the nicotine content of said sample.

8 Claims, No Drawings

METHOD OF DETERMINING THE NICOTINE CONTENT OF TOBACCO

This invention concerns improvements in or relating to the chemical analysis of tobacco or smoking-related products, in particular for the analysis of nicotine content.

In the quality control of cigarettes or other smoking articles it has long been customary to carry out chemical analyses on auto-analyzers of tobacco and other smoking-related products such as filter rod material and cigarette paper. These analyses include analyses for naturally occurring sugars and nicotine in tobacco, glycerol triacetate (triacetin) in cellulose acetate based filter rod material, and citrate salts, which are used as burn modifiers, in cigarette paper.

Hitherto, such analyses have been carried out by a number of laboratory technicians, each assigned to a separate analytical task. It is now proposed to carry out simultaneous chemical analyses of tobacco or tobacco-related products for a number of constituents by means of a discrete analyzer (one example of which being the Technicon RA-1000), such as is used in clinical analysis of physiological samples, but adapted to carry out chemical analyses peculiar to the tabacco industry. The use of a discrete analyzer enable analyses to be carried out simultaneously, more effectively, more accurately, and more consistently, on one machine, than can be carried out by a number of separate analytical processes and operators.

However, there are restrictions imposed by the use of a discrete analyzer, namely that it will not support heating, filtration, dialysis, the use of corrosive materials, or analysis cycles involving lengthy time delays. Although the discrete analyzer is designed to avoid cross-contamination as far as possible, in practice this is difficult to achieve completely, and so the chemical constitution of the reagents used must be such that interaction is minimal. Furthermore, discrete analysis is not a closed system and is open to airborne contamination.

Clearly, chemical analysis procedures hitherto used in the tobacco industry are, in general, quite unsuitable for use simultaneously on a discrete analyzer and so much either be modified or completely changed.

For many years the tobacco industry has used a modification of the Konig reaction in continuous flow analyzers to measure the amount of nicotine present in tobacco and tobacco smoke. In this modified Konig reaction, cyanogen bromide splits the nicotine pyridine ring, and aniline reacts with the reaction product to give a yellow coloration the intensity of which, when measured at a wavelength of 460 nm by spectrophotometric techniques, is directly proportional to the nicotine content of the tobacco or tobacco smoke.

It was found that problems arose when developing the Konig reaction for use on a discrete analyzer. Firstly, nicotine calibration solutions and samples were found to react at different rates, giving rise to erroneous results. Secondly, tobacco smoke extracts were found to give rise to an additional bias, when compared with results from standard methods. Thirdly, the reaction was found to become unstable on the discrete analyzer after approximately one hour of operation.

It is known that the Konig reaction has a formation reaction and a decay reaction, and that the rates of both these reactions are easily upset by temperature, concentration, or contamination by other compounds.

We have now unexpectedly found that a further reaction step becomes apparent when the Konig reaction is used on a discrete analyzer. This further reaction step is that of the protonation of nicotine, which protonation can affect the reliability of analytical results. It is believed that protonated and unprotonated nicotine forms are in equilibrium in solution and have different reaction rates.

It cannot be guaranteed that the equilibrium of tobacco samples and reference standards are the same. Clearly, over the relatively short analysis time used in a discrete analyzer these different reaction rates and equilibria can produce unreliable results. The effect is not noticeable when the Konig reaction is used in a continuous analysis procedure outside a discrete analyzer because the analysis in such circumstances is so slow (relative to the discrete analyzer) that all the critical equilibria are easily attained by natural delay times.

According to the present invention there is provided a method of determining on a discrete analyer the nicotine content of tobacco or a smoking-related product comprising the steps of, (a) preparing an aqueous extract of a sample of tobacco or smoking-related product, (b) pre-reacting the extract with an acidic buffered solution of pH not more than 6 for at least two minutes, (c) reacting the pre-reacted extract in the discrete analyzer with aniline and cyanogen bromide, (d) measuring the intensity of yellow coloration generated by step (c) and generating a first signal proportional to said intensity of coloration of said sample extract, (e) preparing an aqueous extract of a nicotine standard of known nicotine content, (f) carrying out steps (b) and (c) on the extract of step (e), (g) measuring the intensity of yellow coloration produced by step (c) during the performance of step (f) and generating a second signal proportional to said intensity of said standard extract, and (h) comparing said first and second signals to determine the nicotine content of said sample.

The aqueous extract is preferably prepared by acid extraction of the tobacco or smoking-related product. The acid may be a 1% solution of acetic acid in water. When the sample is tobacco the acidic buffered solution is preferably based on citric acid.

When the sample is a smoking-related product other than tobacco, such as tobacco smoke, the acidity of the acidic buffered solution is preferably not more than 4 pH and the time taken for the pre-reaction is preferably at least four minutes. When the acidity of the acidic buffered solution is not more than 4 pH the acid is preferably hydrochloric acid.

The nicotine standard is preferably nicotine hydrogen tartrate.

The intensity of the yellow coloration is preferably measured spectrophotometrically at a wavelength of 460 nm.

The invention will now be described with reference to the following non-limiting examples.

EXAMPLE 1

An extraction solution A containing 1% acetic acid and 2% invertase concentrate was prepared by making 10 ml acetic acid and 20 ml invertase concentrate up to 1 liter with water. The invertase concentrate was a proprietary mixture of invertase, water and glycerol.

0.400 grams of a tobacco sample were shaken with 100 ml of solution A for 20 minutes, and filtered to provide extract B prior to analysis on a discrete analyzer at room temperature.

During extraction of the tobacco by solution A, the acetic acid removes the nicotine from the tobacco into solution as nicotine acetate. The purpose of the invertase is to convert surcrose in the tobacco to glucose and fructose, in readiness for subsequent analysis of the sugar content of the tobacco; the invertase is otherwise irrelevant as far as nicotine analysis is concerned. The mixture of tobacco and acetic acid has pH 4–5, although the pH of solution A before the tobacco is added is less than pH 4.

An acidic buffer solution C of pH 6.0 for the pre-reaction of extract B was prepared by dissolving 28.36 g di-sodium hydrogen orthophosphate and 8.2 g citric acid in 900 ml distilled water, adding 3 ml analytical reagent quality redistilled aniline, making up to 1 liter with distilled water and adding 10 ml of 25% TRITON X-405 (Trade Mark) wetting agent.

A nicotine reagent D was prepared by dissolving 3.0 g cyanogen bromide in 100 ml 1:1 propan-2-ol/distilled water.

In the discrete analyzer 6.5 microliters of extract B were added to 350 microliters of pH 6.0 buffer solution C. After 4 minutes 100 microliters of cyanogen bromide solution D were added to the mixture of solutions B and C. After a delay of 2 minutes the intensity of the yellow coloration produced was measured at 460 nm spectrophotometrically and a signal indicative of the intensity passed to a microcomputer.

The same procedure was carried out using a nicotine hydrogen tartrate of known concentration as a standard instead of the tobacco sample, and a second signal indicative of the intensity of the yellow coloration produced by the reaction of the cyanogen bromide with the buffered nicotine hydrogen tartrate was passed to the microcomputer. The microcomputer then determined the percentage of nicotine in the tobacco sample from a comparison of the two signals.

EXAMPLE 2

An extraction solution A was made up as in Example 1, and a sample of tobacco smoke was extracted by A to produce a nicotine acetate extract B1 as in Example 1.

An acidic buffer solution C1 of pH 4.0 for the pre-reaction of extract B1 was prepared as follows. 16.4 g of anhydrous sodium acetate was dissolved in 900 ml distilled water. 6.0 ml of concentrated hydrochloric acid were added and the mixture swirled. 3 ml analytical reagent quality redistilled aniline were then added and the mixture made up to 1 liter with distilled water and 10 ml of 25% TRITON X-405 (Trade Mark) wetting agent finally added.

A nicotine reagent D was prepared as in Example 1.

In the discrete analyzer 10 microliters of extract B1 were added to 350 microliters of pH 4.0 buffer solution C1. After 4 minutes 100 microliters of cyanogen bromide solution D were added to the mixture of solutions B1 and C1. After a delay of 4 minutes 45 seconds the intensity of the yellow coloration produced was measured at 460 nm spectrophotometrically and a signal indicative of the intensity passed to a microcomputer.

As in Example 1, the procedure of Example 2 was carried out on a nicotine hydrogen tartrate standard solution, and a second signal indicative of the intensity of the yellow coloration produced was passed to the mirocomputer. The percentage of nicotine present in the smoke sample was then determined from a comparison of the two signals.

The chemical reagents used to put into effect these reactions are commonly held within discrete analyzers in containers made of polymeric materials (i.e. plastics materials such as nylon or polyethylene). The concentration of cyanogen bromide, in particular, was found to influence the rate of colour formation and was shown to be depleted by reaction with new polymer surfaces. This was found to have the effect of destabilising the reaction after approximately one hour of continuous use. This was overcome by initially passivating the container for cyanogen bromide by means of a high concentration cyanogen bromide solution being allowed to contact the interior surface of the container for a minimum of 24 hours before use.

The efficacy of the method of the invention was compared with that of a hitherto known method (Auto-Analyser) using statistical techniques. In this comparison 'DA' will be taken to mean a Discrete Analyser, and 'AA' will be taken to mean an Auto-Analyser.

50 individual tobacco samples were chosen for assessment of percentage content of rag nicotine. These sample tobaccos covered a range of flue, oriental and air cured varieties containing from 0.1 to 7% nicotine and 0 to 35% sugar.

20 cigarette types were chosen for assessment of smoke and tip nicotine content. These cigarette types covered a range of particulate matter (0.1 to 25 mg/cig), nicotine (0.1 to 4 mg/cig) and water (0 to 10 mg/cig), and included both flue and blended tobaccos.

Bulks of each tobacco and cigarette type were chosen to be sufficient to allow a total of eight random order analyses by both the DA and the AA.

Each tobacco bulk sample was milled as a whole and divided randomly into eight sub-samples. From each sub-sample, test samples were prepared as follows and then analysed in random order on AA and DA as appropriate.

AA: 0.4 g were taken from the sub-sample and extracted with 100 ml dilute sulphuric acid.

DA: 0.4 g were taken from the sub-sample and extracted with 25 ml dilute acetic acid/invertase.

For the cigarette analyses randomised order machine smokings using cambridge filter pads were performed. Eight sub-samples of each cigarette type were formed and smoke condensate obtained from a single channel smoking consisting of five replicate cigarettes.

For each cigarette type, and separately from the cambridge filter pad and the cigarette tips, extraction was carried out with 20 ml propanol. 5 ml were then diluted with sulphuric acid for analysis by AA, and the remaining propanol extract was used directly by the DA.

The analytical results were statistically examined for variance and analysis of variance (F-values with confidence limits). The statistical analyses are set out in Tables 1 to 4 and show that the Discrete Analyzer method of the present invention produces significantly more reliable results than the method of the Auto-Analyzer.

TABLE 1

| | CIGARETTES | | | |
| --- | --- | --- | --- | --- |
| | TIP NICOTINE | | SMOKE NICOTINE | |
| VARIANCES | AA | DA | AA | DA |
| Sample | 0.00211 | 0.00080 | 0.00122 | 0.00111 |

TABLE 2

| | TOBACCO | |
| --- | --- | --- |
| | % NICOTINE | |
| VARIANCES | AA | DA |
| Sample | 0.00037 | 0.00065 |

TABLE 3

Analysis of variance on tobacco data (F-values and significance level).

| | NICOTINE | |
| --- | --- | --- |
| | F-value | Sig. lev. |
| Sample | 148.52 | 0.1% |

TABLE 4

Analysis of variance on cigarette data (F-value and significance level).

| | TIP NICOTINE | | SMOKE NICOTINE | |
| --- | --- | --- | --- | --- |
| | F-value | Sig. lev. | F-value | Sig. lev. |
| Sample | 235.66 | 0.1% | 142.06 | 0.1% |

We claim:

1. A method of determining on a discrete analyzer the nicotine content of tobacco or a smoking-related product wherein the discrete analyzer includes a container for cyanogen bromide made of a polymeric material, the method including a prior step of passivating the container to cyanogen bromide by allowing a cyanogen bromide solution of high concentration to contact the interior of the container for a period of at least 24 hours before the first use of the container in the method, and including the further steps of, (a) preparing a first aqueous extract of a sample of tobacco or smoking-related product, (b) pre-reacting the extract with an acidic buffered solution of pH not more than 6 for at least two minutes, (c) reacting the pre-reacted extract in the discrete analyzer with aniline and with cyanogen bromide from the passivated container, (d) measuring the intensity of yellow coloration generated by step (c) and generating a first signal proportional to said intensity of coloration of said sample extract, (e) preparing a second aqueous extract of a nicotine standard of known nicotine content, (f) carrying out steps (b) and (c) on the extract of step (e), (g) measuring the intensity of yellow coloration produced by step (c) during the performance of step (f) and generating a second signal proportional to said intensity of said standard extract, and (h) comparing said first and second signals to determine the nicotine content of said sample.

2. The method as claimed in claim 1 wherein, when the sample is tobacco, the acidic buffered solution is based on citric acid.

3. The method as claimed in claim 1 wherein the nicotine standard is nicotine hydrogen tartrate.

4. The method as claimed in claim 1 wherein the intensity of the yellow coloration is measured spectrophotometrically at a wavelength of 460 nm.

5. The method as claimed in claim 1 wherein the first aqueous extract is prepared by acid extraction of said tobacco or smoking-related product.

6. The method as claimed in claim 5 wherein said acid of the first aqueous extraction step comprises is 1% v/v solution of acetic acid in water.

7. The method as claimed in claim 1 wherein, when the sample is a smoking-related product other than tobacco, the acidity of the acidic buffered solution is not more than 4 pH and the time taken for the pre-reaction is at least four minutes.

8. The method as claimed in claim 7 wherein the acid buffered solution comprises hydrochloric acid.

* * * * *